United States Patent [19]

Salyers

[11] Patent Number: 5,423,581

[45] Date of Patent: Jun. 13, 1995

[54] LOW CARRYOVER FITTING AND METHOD FOR COUPLING TUBING TO A DEVICE USING THE SAME

[76] Inventor: Marshall L. Salyers, 641 S. Warren Ave., Malvern, Pa. 19355

[21] Appl. No.: 40,426

[22] Filed: Mar. 31, 1993

[51] Int. Cl.⁶ ............................................. F16L 19/00
[52] U.S. Cl. ................... 285/382; 285/219; 285/159; 285/382.7; 285/353
[58] Field of Search ............ 285/382, 382.7, 245, 285/246, 247, 248, 353, 343, 219, 220, 159

[56] References Cited

U.S. PATENT DOCUMENTS

| | | | |
|---|---|---|---|
| 1,968,368 | 7/1934 | Bredeson | 285/219 |
| 2,321,260 | 6/1943 | Stecher | 285/382.7 |
| 2,591,326 | 4/1952 | Williams | 285/246 |
| 2,737,403 | 3/1956 | Ellis | 285/382.7 |
| 3,006,664 | 10/1961 | Appleton et al. | 285/382.7 |
| 3,025,086 | 3/1962 | Mosely | 285/750 |
| 3,030,129 | 4/1962 | Appleton | 285/382.7 |
| 3,362,731 | 1/1968 | Gasche et al. | 285/219 |
| 3,368,837 | 2/1968 | Phillipps | 285/382.7 |
| 4,000,918 | 1/1977 | Reker | 285/248 |
| 4,033,614 | 7/1977 | Hanson | 285/248 |
| 4,192,532 | 3/1980 | Pacella | 285/382.7 |
| 4,614,372 | 9/1986 | Gschwind | 285/353 |
| 4,877,271 | 10/1989 | McCorkle et al. | 285/220 |

FOREIGN PATENT DOCUMENTS

| | | | |
|---|---|---|---|
| 1208788 | 2/1960 | France | 285/246 |
| 434148 | 6/1949 | Italy | 285/246 |
| 1227282 | 4/1971 | United Kingdom | 285/246 |

OTHER PUBLICATIONS

LFDA Series, Miniature Solenoid Valves; from the Fifth Edition of Lee Electro-Fluidic Systems 1991; pp. 81–91 and 94–136; Publication of Lee Company, Westbrook, Conn. 06498.

Lee Company Fitting Assemblies; from the Second Edition of The Lee Instac/LIF Handbook, 1982; pp. 47–66; Publication of the Lee Company, Westbrook, Conn. 06498.

Primary Examiner—Eric K. Nicholson
Attorney, Agent, or Firm—Ratner & Prestia

[57] ABSTRACT

A low carryover fitting assembly for coupling tubing to a device having a sealing surface is presented. The fitting includes a ferrule having a conical head for seating against the sealing surface. The ferrule has a conical tail. The ferrule has an axial passage that is substantially equal in diameter to the inside diameter of the tubing. The fitting includes a sleeve having a ramped inner surface that is greater in inside diameter towards the forward end of the sleeve and smaller in inside diameter towards a rearward end of the sleeve. The fitting also includes a coupler, such as a coupling nut. The coupler has a front surface that engages the head of the ferrule to push the head against the sealing surface. The nut has an inner ramp or shoulder that engages the sleeve to urge the sleeve towards the head of the ferrule when the coupling nut is tightened. The tubing is compressed between the tail of the ferrule and the tapered section of the sleeve. The tubing is compressed so that it flows to a region between the tail and the ramped inner surface.

36 Claims, 14 Drawing Sheets

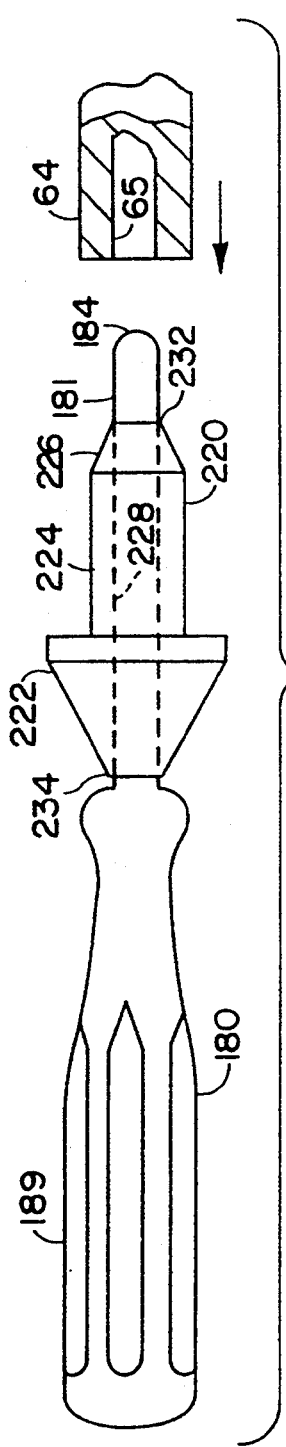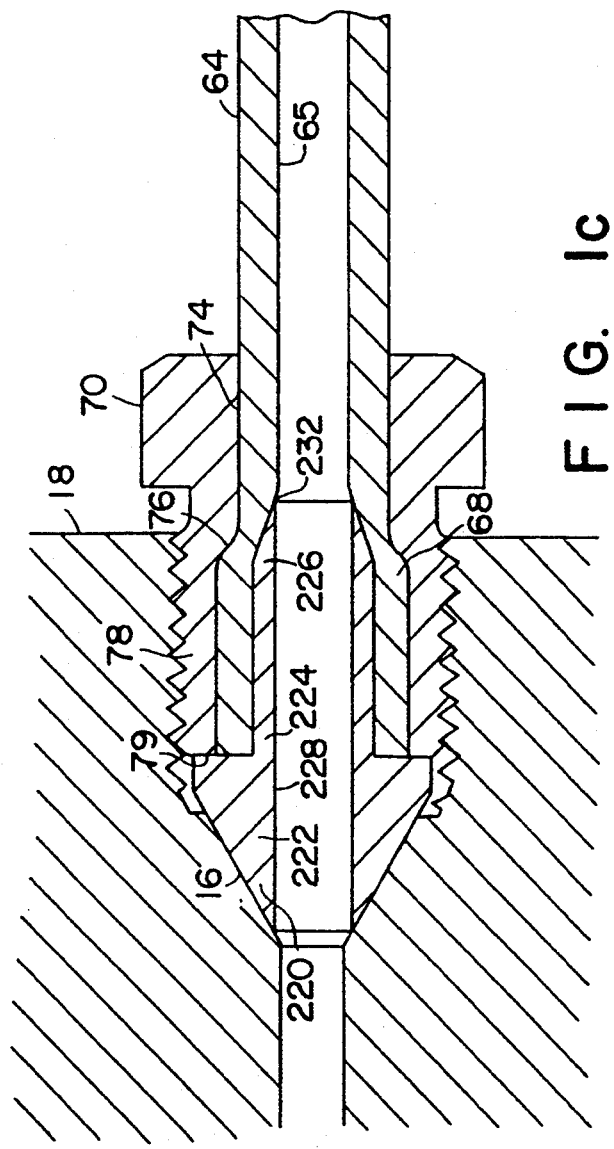

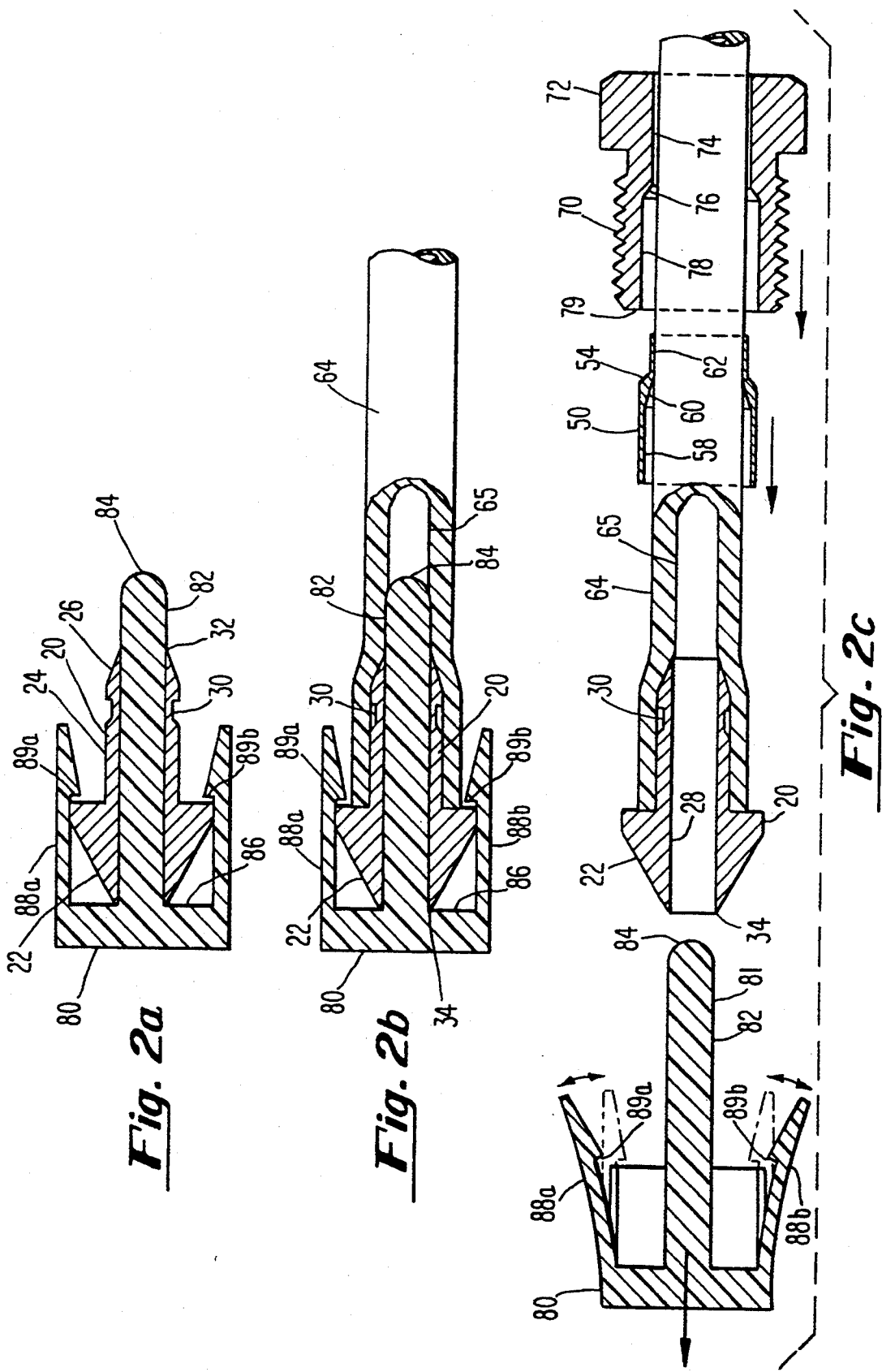

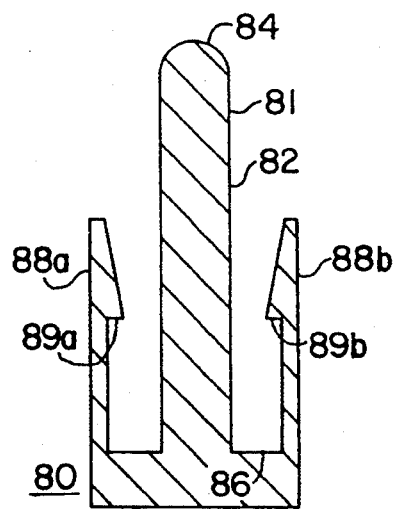
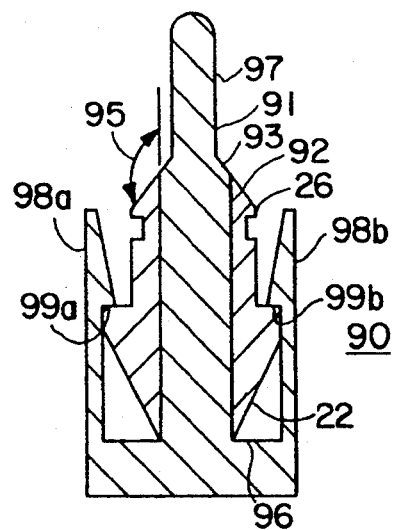
FIG. 6    FIG. 7
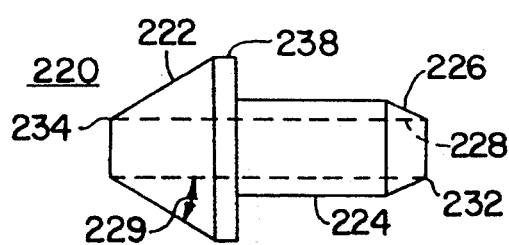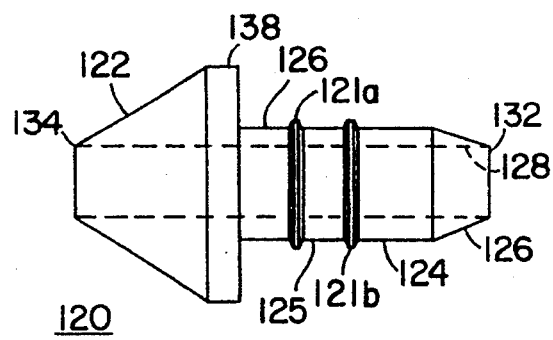
FIG. 8a    FIG. 8b
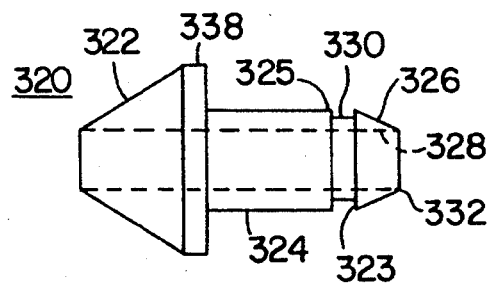
FIG. 8c

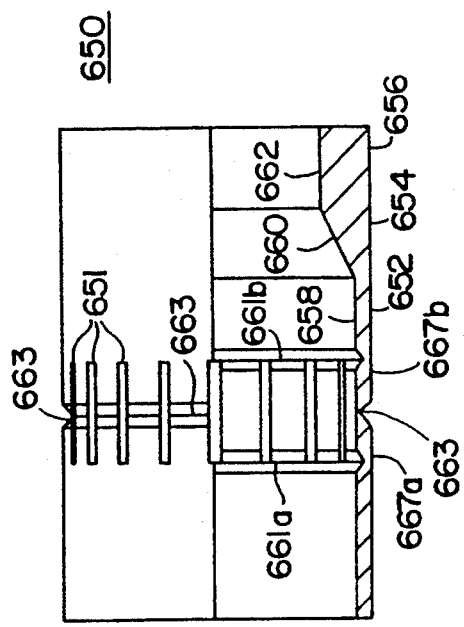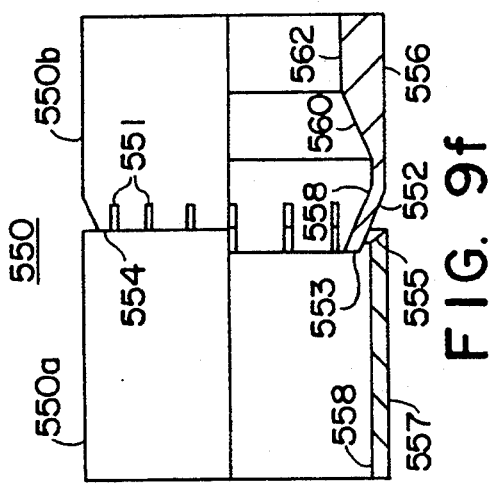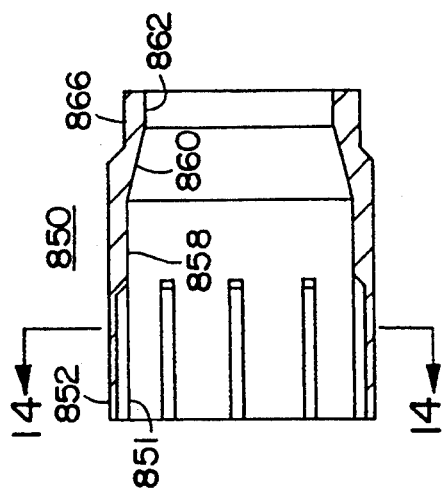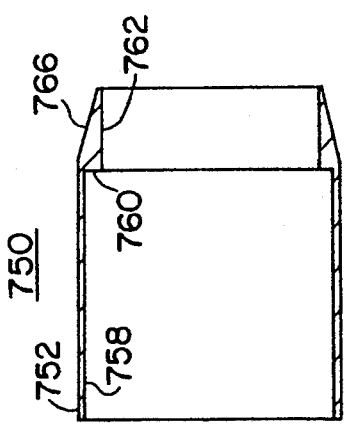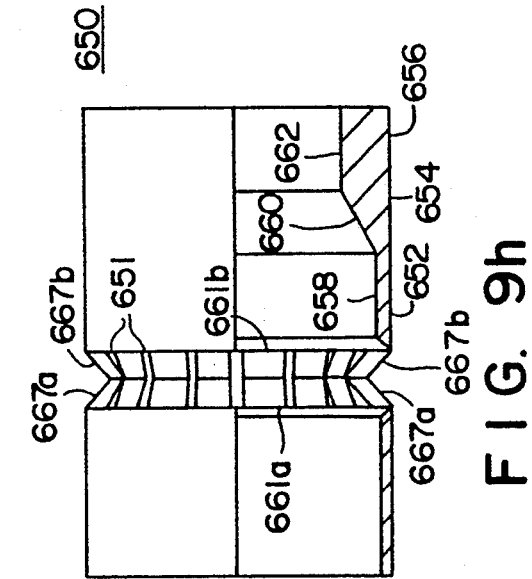

LOW CARRYOVER FITTING AND METHOD FOR COUPLING TUBING TO A DEVICE USING THE SAME

FIELD OF THE INVENTION

The present invention relates to fittings for fluidic device applications.

BACKGROUND OF THE INVENTION

Low carryover fittings are required to couple tubing to a device in many applications. For example, a fitting may be used to handle corrosive fluid or gas in an inert manner, or to connect tubing to a blood chemistry analyzer, medical chemical analyzer, DNA research equipment, chromatography equipment, nuclear atomic trace equipment, or other precision fluidic application.

For these applications, the fitting must provide a leak proof connection with substantially zero carryover. Carryover occurs when there is a non-flushable dead volume in a system flow passage or component, which typically occurs when there is an abrupt change in diameter in the passage or component. The dead volume is the quantity of the sample retained inside the passage after flushing with a specified volume. This dead volume may retain material to contaminate subsequent samples or fluids. For the applications listed above, carryover is unacceptable.

As shown in FIG. 11, typical prior art ferrules, such as ferrule 1320 have a tail section 1326 with a blunt end 1326a. Alternatively, tail 1326 may have a rounded corner 1326b. When tubing 1364 is forced over the blunt end 1326 of ferrule 1320, there is a large dead volume 1369, resulting in substantial carryover, even if the passage 1328 is flushed.

A known low carryover fitting for use with tetraflouroethylene (TFE) tubing is the 125 Minstac fitting manufactured by the Lee Company of Westbrook, Conn. The fitting includes an internally threaded collet or sleeve that grips the outer diameter of the tubing end. The end of the tubing is chamfered to receive a ferrule having a cone shaped tail that is received by the chamfer in the tubing. The ferrule has an inner passage that is approximately 0.002 inches less in diameter than the tubing, to provide a low dead volume where the two meet. The ferrule also has a cone shaped head that seats against a chamfered sealing surface in the device. A coupling screw acts like a compression fitting and presses the chamfered end of the tubing against the tail of the ferrule.

Several steps are involved in the use of the Minstac fitting. In order to use the fitting, a special tool called a collet tool is needed to crimp the collet onto the tubing. A second tool, called a chamfer tool, is used to chamfer the tubing. This may be particularly difficult with slippery tube materials such as TFE. In order to provide sufficient compression to form a seal between the tubing and the device, without damaging the tubing or the ferrule, the coupling screw must be tightened within a limited range of torque. Typically a special torque wrench is used to tighten the coupling screw. If excessive torque is applied, the ferrule may push the tubing out of the collet. Furthermore, soft tubing materials, such as TFE composites, can deform inward, so that the collet may not grip them securely enough.

A low carryover fitting is desired that is simple to install and requires no special tools. It is also desired that the fitting includes a mechanism to prevent damage due to excessive torque.

SUMMARY OF THE INVENTION

The invention is a low carryover fitting assembly for coupling tubing to a device having a sealing surface.

The fitting includes a ferrule that seats against the sealing surface. The ferrule has a head, a body and a tail. A coupler is provided for engaging the ferrule to push the head against the device. The coupler includes an inner surface. A region is defined between the coupler and the body of the ferrule. The tubing material is compressed between the tail of the ferrule and the inner surface. The compression causes the tubing material to flow into the region.

BRIEF DESCRIPTION OF THE DRAWINGS

FIG. 1b is an elevation view of the fitting shown in FIG. 1a, during assembly.

FIG. 1c is a cross sectional view of the fitting of FIG. 1a, installed in a device.

FIGS. 2a-2c are cross sectional views of a second embodiment of the invention, during different stages of assembly.

FIGS. 3b-3d are enlarged cross sections of features of the embodiment of FIG. 3a.

FIG. 6 is a cross sectional view of the holder shown in FIGS. 5a and 5b.

FIG. 7 is a cross sectional view of an alternative embodiment of the holder shown in FIG. 6, and the ferrule shown in FIG. 4a.

FIGS. 8a-8l are elevation views of alternative embodiments of the ferrule shown in FIG. 4a.

FIGS. 9e-9h are partial cross sectional views of two additional embodiments of the sleeve shown in FIG. 4c.

FIGS. 9a and 9j are cross sectional views of additional/variations of the sleeve shown in FIG. 4c.

DETAILED DESCRIPTION OF THE INVENTION

Overview

Figure 1A:
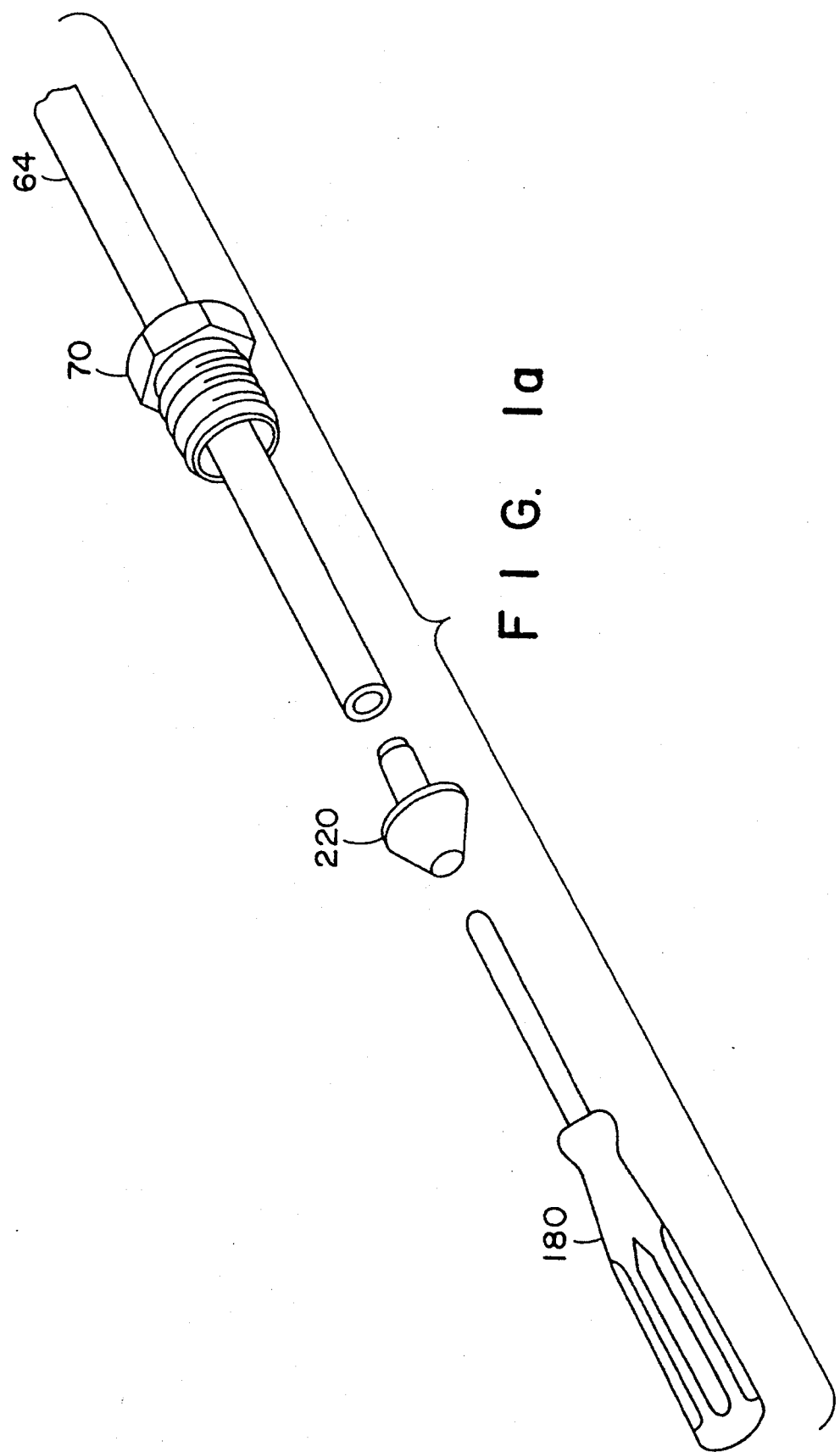
FIG. 1a is an exploded perspective view of a fitting and installation tool according to the invention.

FIG. 1a is an exploded perspective view of an exemplary low carryover fitting assembly in accordance with the invention. The fitting includes a ferrule 220 and a coupler 70 in the form of a nut that provides a means for coupling a section of tubing 64 to a chamfered sealing surface 16 of device 18 (shown in FIG. 1c). Device 18 may be a blood chemistry analyzer, a medical chemical analyzer, DNA research equipment, chromatography equipment, nuclear atomic trace equipment, or other precision fluidic apparatus. An assembly tool 180 is used to hold and protect ferrule 220 during tubing installation and to align the tubing 64, as explained below with reference to FIG. 1b.

FIG. 1b is an exploded elevation view showing ferrule 220 in place on shaft 181 of tool 180. Ferrule 220 is also shown in elevation view in FIG. 8a. Ferrule 220 has a tapered head 222 that seats against the chambered sealing surface 16 within a conventional bore of device 18 (shown in FIG. 1c). Ferrule 220 has a tapered tail 226 terminating in a knife sharp edge 232, and a body 224 integrally connecting the head 222 and the tail 226. The ferrule 220 has an axial passage 228 that is at least as large in diameter as the inside diameter 65 of the tubing 64, and may be up to about 3% larger than the nominal size of the tubing.

Tool 180 has a shaft 181 that extends through the axial passage 228 of ferrule 220. Shaft 181 has a rounded tip 184. It is contemplated that the invention may be practiced using other tapered tip profiles. Shaft 181 is longer than ferrule 220, and larger in diameter than the inside diameter 65 of tubing 64 by 0.002–0.004 inches. The shaft 181 may be formed of any suitably hard material, and the handle 189 shape is optional.

The end of tubing 64 is cut square; no chamfer is needed. This cutting operation may be performed with an ordinary knife or razor. To assemble the fitting, coupling nut 70 is slipped onto the tubing 64. Then tubing 64 is gripped, either using a bare hand, or a piece of grit cloth. Tubing 64 is pushed over the tip 184 of the shaft 181. This guides the tubing 64 to the outer surface of the tail 226 of ferrule 220. Tubing 64 is pushed further, till it surrounds body 224 and tail 226 of ferrule 220. Then, tool 180 is removed, and coupling nut 70 is slid over tail 226 and body 224 of ferrule 220.

As shown in the example of FIG. 1c, coupler 70 may be in the form of a nut having a cylindrical rearward section 74 that is smaller in inside diameter than forward section 78. Coupling nut 70 has a ramped inner surface 76 integrally connecting the forward and rearward sections 78 and 74. Coupling nut 70 has a front surface 79 that engages the head 222 of ferrule 220 to push the head 222 against surface 16 of device 18. Tubing 64 is compressed between tapered shoulder 76 of nut 70 and tail 226 of ferrule 220, when coupling nut 70 is tightened, cold flowing tubing 64. FIG. 1c is a cross sectional view showing the configuration of the fitting after it is inserted into chamfered sealing surface 16 of device 18 and tightened. Tubing material flows in region 68 between body 224 of ferrule 220 and forward section 78 of coupling nut 70, forming an enlarged annular ring of tubing material around body 224 of ferrule 220. The enlarged annular ring in region 68 effectively prevents tubing 64 from being pulled out.

Figure 2D:
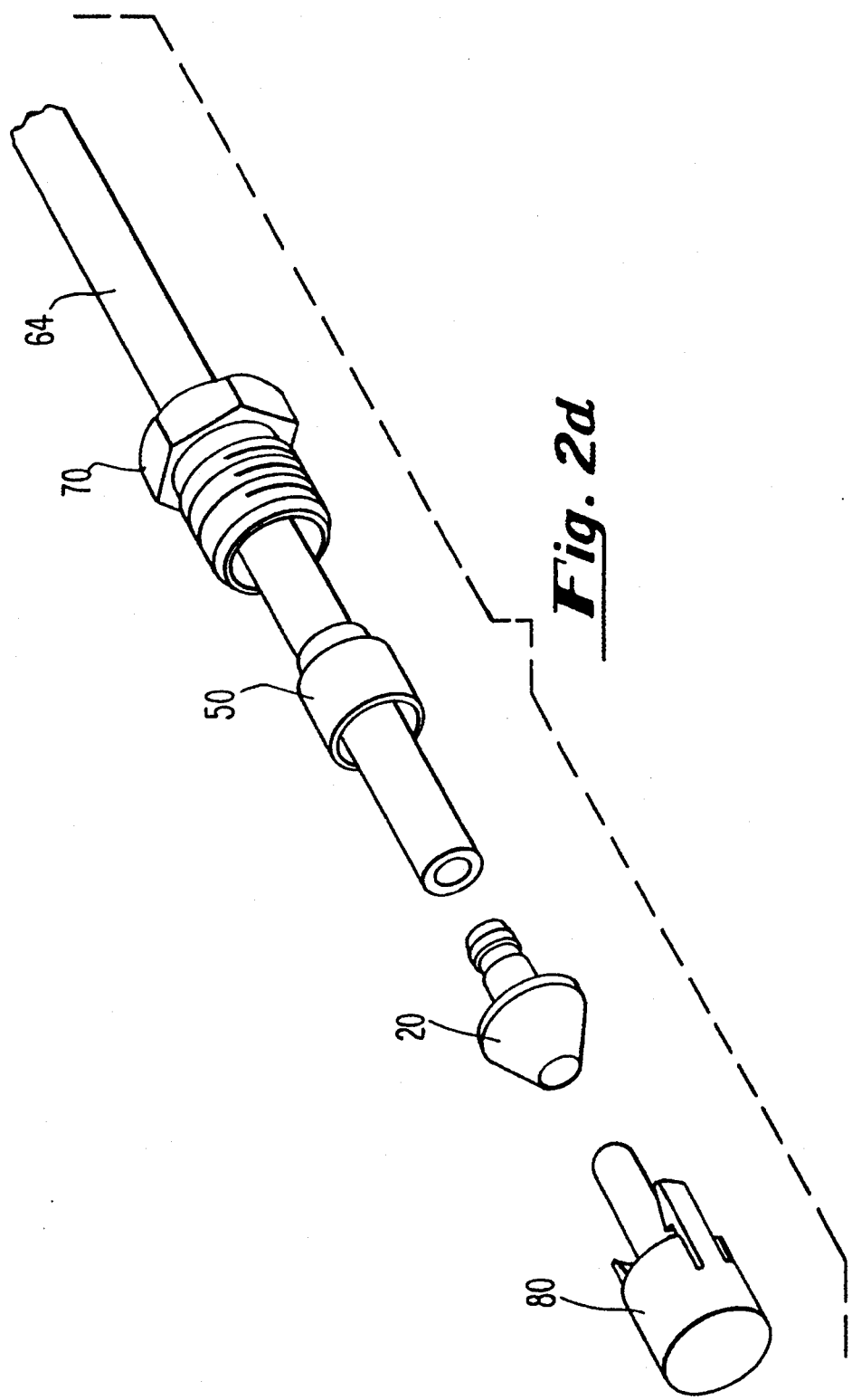
FIG. 2d is an exploded perspective view of the embodiment of the invention shown in FIGS. 2a-2c.

FIG. 2d is an exploded perspective view of a second embodiment of the invention. The fitting includes a ferrule 20, a sleeve 50 and a coupling nut 70 for coupling a section of tubing 64 to a device 18 (shown in FIG. 3a). In this embodiment of the invention, the coupling means include coupling nut 70 and sleeve 50 (compared to the embodiment of FIG. 1a, in which the coupling means only includes nut 70). Sleeve 50 substantially prevents twisting of the tubing 64 by coupling nut 70 when nut 70 is tightened. A holder 80 is used to hold and protect ferrule 20 during handling, and plays an additional role in installing ferrule 20 in the tubing 64, as explained below with reference to FIGS. 2a through 2c.

FIG. 2a is a cross sectional view of an exemplary ferrule 20 in its holder 80, before the fitting is attached to tubing 64. Ferrule 20 is also shown in elevation view in FIG. 4a. Features that are identical in ferrule 20 and ferrule 220 have reference numerals with the same last two digits, for ease of comparison.

Referring to FIG. 2a, holder 80 has a front wall 86 against which the head 22 of the ferrule 20 seats. A side wall 87 (shown in FIG. 5b) substantially surrounds the head 22 of ferrule 20 to protect the head 22. Holder 80 has a shaft 81 that extends through the axial passage 28 of ferrule 20. Shaft 81 has a proximal portion 82 and a tip 84. The proximal portion 82 of the shaft is longer than ferrule 20, and substantially equal to the tubing inside diameter or larger in diameter than the inside diameter 65 of tubing 64 by a few percent.

To assemble the fitting, coupling nut 70 and sleeve 50 (shown in FIG. 2c) are slipped onto the tubing 64. Then tubing 64 is gripped and pushed over the tip 84 of the shaft 81. This guides the tubing 64 to the outer surface of the tail 26 of ferrule 20. Tubing 64 is pushed further, till it surrounds body 24 and tail 26 of ferrule 20, as shown in FIG. 2b. Then, as shown in FIG. 2c, the latches 89a and 89b of holder 80 are pulled apart, releasing ferrule 20. The holder is removed and may be discarded. Sleeve 50 and coupling nut 70 are slid over the tail 26 and body 24 of ferrule 20.

As shown in FIG. 2c, sleeve 50 has a cylindrical rearward section 62 that is smaller in inside diameter than forward section 58. Sleeve 50 has a shouldered outer surface 54 and a ramped inner surface 60 integrally connecting the internal diameters of forward and rearward sections 58 and 62. Sleeve 50 may also have a cylindrical forward section 58 that is shorter in length than the body 24 of ferrule 20, as shown. In this embodiment, tubing is compressed between tail 26 of the ferrule and the ramped inner surface 60 of the sleeve. A region is defined between the coupling means and body 24 of ferrule 20, specifically, between sleeve 50 and body 24.

Figure 3A:
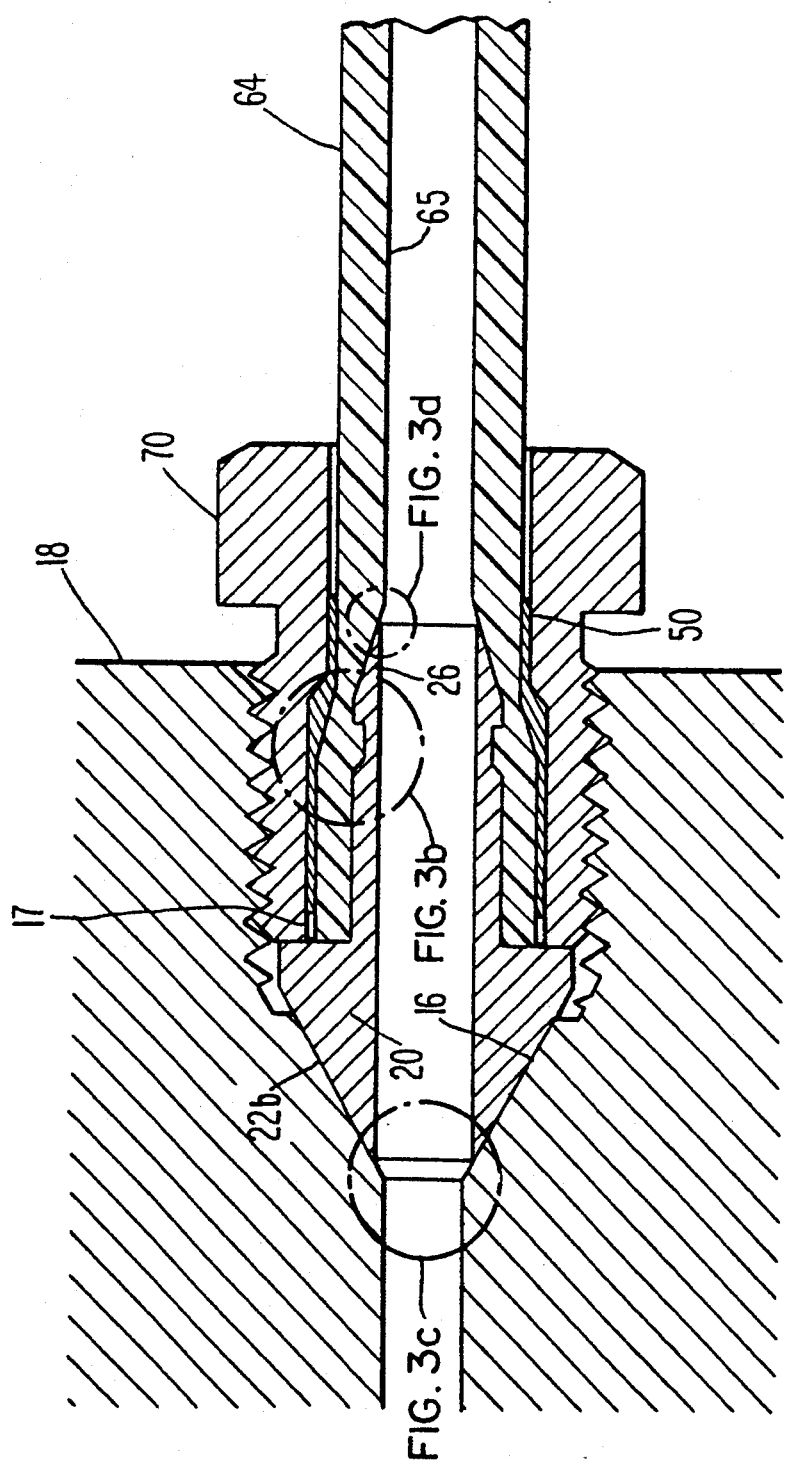
FIG. 3a is a cross sectional view of the fitting of FIG. 2d, installed in a device.

Front surface 79 of coupling nut 70 engages head 22 of ferrule 20 to push head 22 against surface 16 of device 18 (shown in FIG. 3a). Inner shoulder 76 of nut 70 engages the shouldered outer surface 54 of sleeve 50, to move sleeve 50 towards the head 22 of ferrule 20 when coupling nut 70 is tightened. FIG. 3a is a cross sectional view showing the configuration of the fitting after it is inserted into device 18 and tightened. Tubing 64 is compressed between tail 26 of ferrule 20 and the ramped inner surface 60 of sleeve 50. By adding sleeve 50, radial twisting of tubing 64 is avoided. Nut 70 pushes sleeve 50 forward without rotating sleeve 50 about its longitudinal axis.

The assembly, as described with reference to FIGS. 1a–1c and 2a–2d, has several advantages over the fittings of the prior art. Ferrules 20 and 220 are formed of titanium, or other suitably hard material, that does not yield while nut 70 is tightened over a wide range of torques. Thus, coupling nut 70 may be tightened with a conventional wrench (instead of a customized torque wrench) without harming the ferrule 20, 220 or the seal. Because they are used below their yield stress, ferrules 20 and 220 are reusable.

Figure 3B:
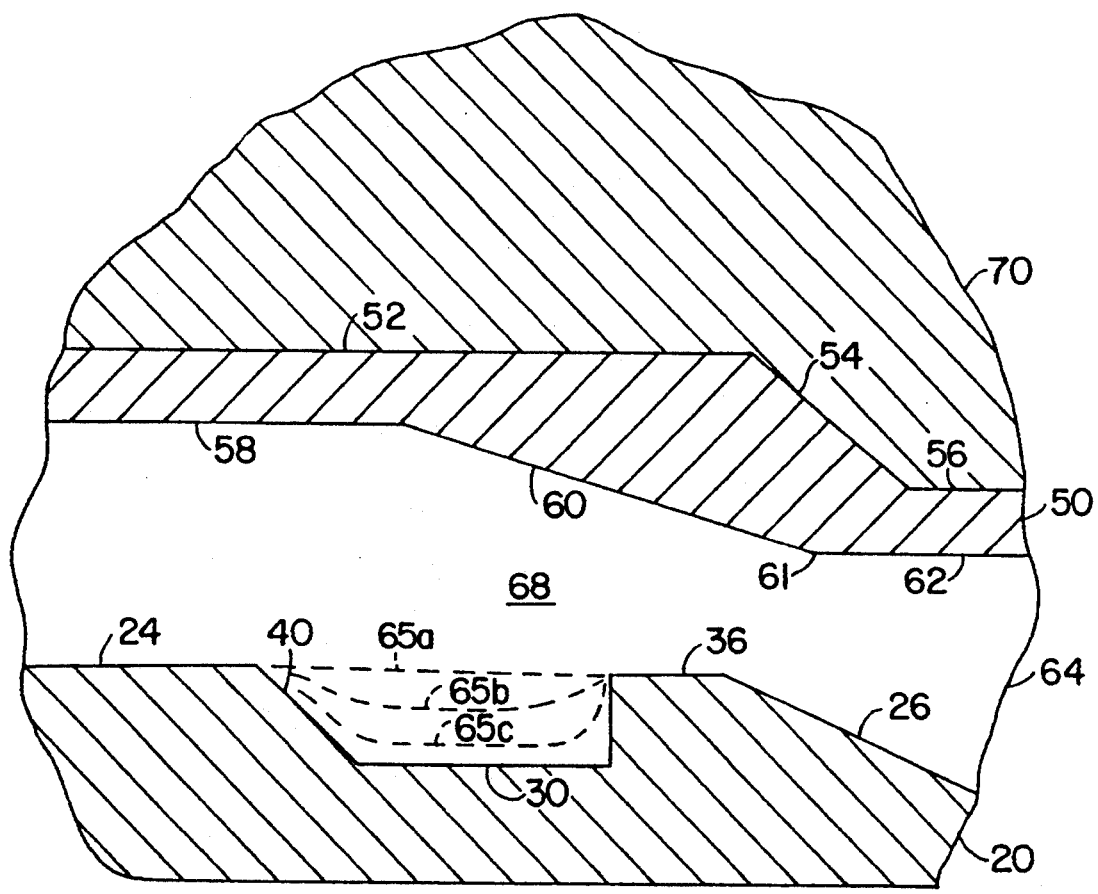
Figure 3C:
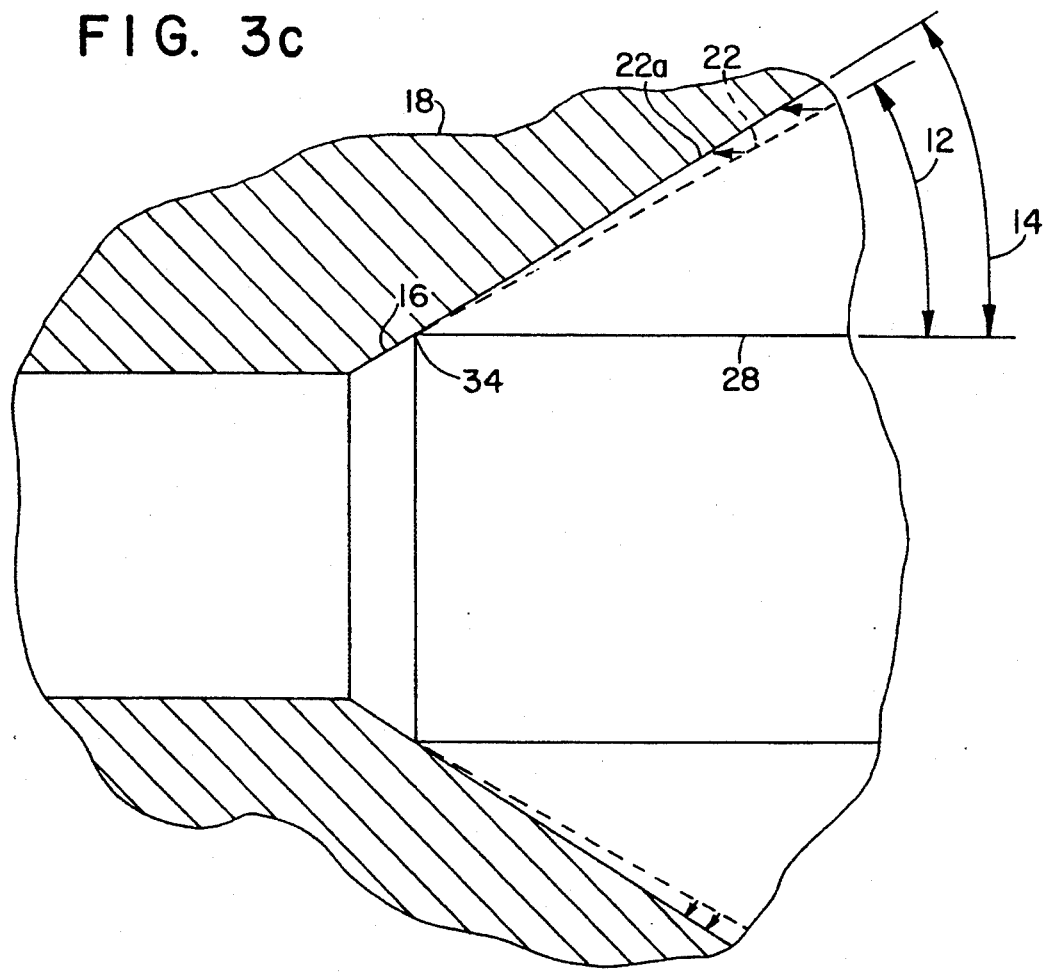
Figure 3D:
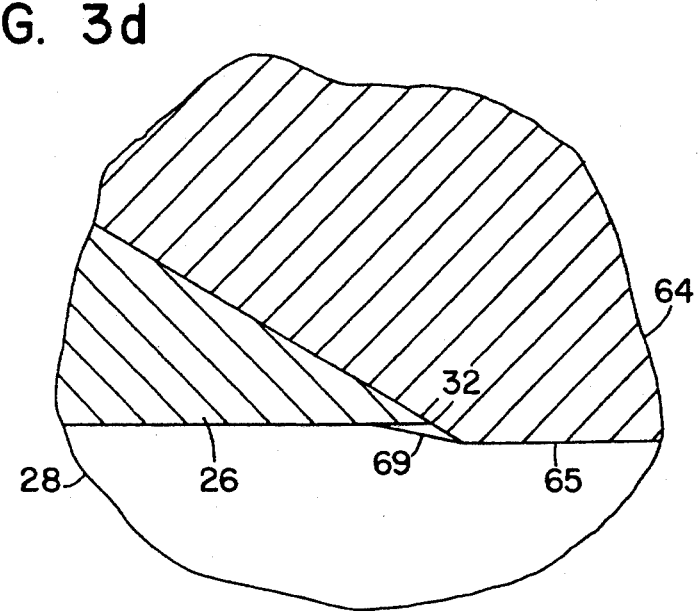
Figure 11:
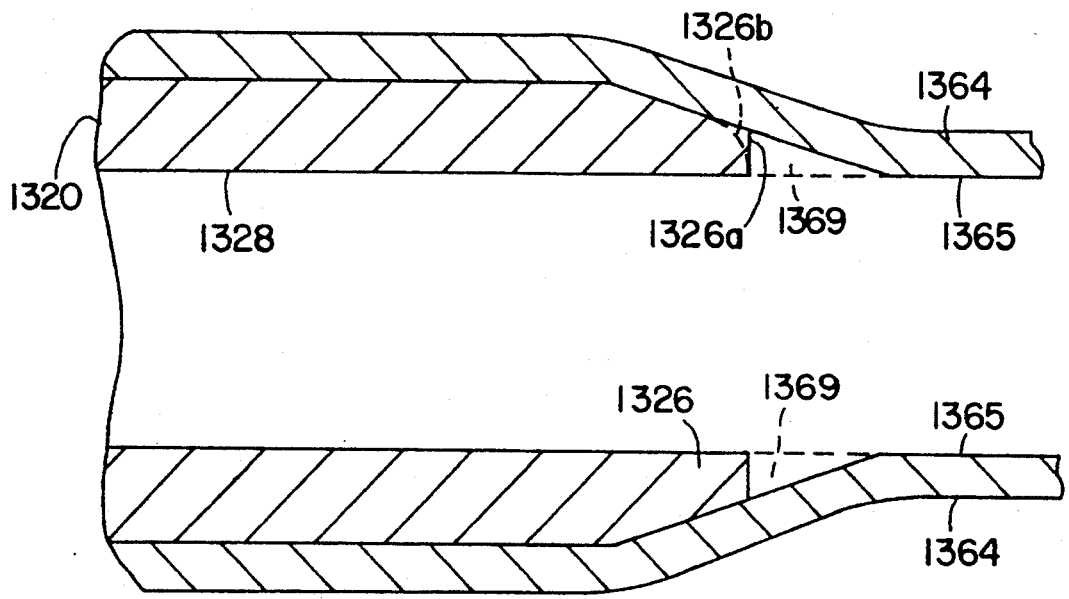
FIG. 11 shows an enlarged feature of a typical prior art fitting.

FIG. 3d is an enlarged cross sectional view of the sharp edge 32 of tail 26 of ferrule 20. The diameter of passage 28 is equal to the inner diameter 65 of tubing 64, or larger than diameter 65 by a minimal amount, such as 0.002 inches. The edge 32 of tail 26 is sharp. Thus, there is substantially zero dead volume 69 at the edge 32 of tail 26. This feature of the invention results in a fitting with substantially zero carryover, in contrast to the prior art ferrule, shown in FIG. 11.

Because of the sharp edge 32 on tail 26, holder 80 plays an important role in protecting ferrule 20 from damage during shipping and handling. Both holder 80 and tool 180 play an additional role in protecting the tubing 64 during assembly. The material of tail 26 is very thin at the rearward end 32. Shaft 82 of holder 80 is long enough to align the tubing concentric with shaft 82 and ferrule 20. The concentric alignment and the small clearance between shaft 82 and the tail 26 of ferrule 20 allow tubing 64 to be pushed over the edge 32 of ferrule 20 without gouging inner wall 65 of tubing 64. Holder shaft 81 (or tool shaft 181) prevents gouging of tubing 64 and permits use of a knife sharp edge 32; this in turn results in low dead volume 69 for substantially zero carryover.

FIG. 3b is an enlarged cross sectional view showing how tubing 64 deforms to create an effective seal when ferrule 20 is used. When coupling nut 70 is tightened, tubing 64 is compressed between an inside corner 61 of sleeve 50 and the tail 26 of ferrule 20. When tubing 64 is initially pushed over ferrule 20, the tubing is substantially straight, as shown in phantom by surface 65a. After tightening, the pressure from the compressed region of tubing 64 causes the tubing material to flow into region 68 and into groove 30, as shown in phantom by surfaces 65b and 65c. The combination of the compressed tubing between corner 61 and tail 26, and the cold flowed material in region 68 that flows into groove 30 grips tubing 64 so firmly that if subjected to severe tensile loading, no leakage occurs at the fitting, and the tubing 64 yields until it fails in tension, rather than being pulled out of the fitting. Typically, in either prior art low carryover fittings or conventional plastic tubing fittings, the tubing can be pulled partially out of the fitting, causing leakage, or pulled completely out of the fitting without any yielding occurring.

The Exemplary Embodiments

The Ferrule

Figure 4A:
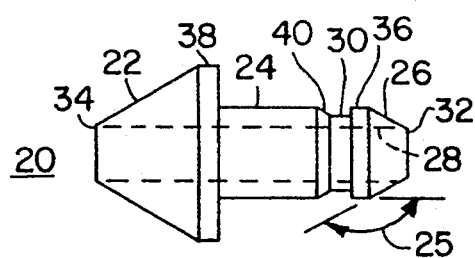
FIG. 4a is an elevation view of the ferrule shown in FIG. 2d.
Figure 8D:
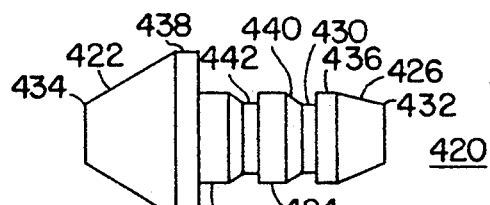

FIG. 8a is an elevation view of an embodiment of a ferrule 220 in accordance with the invention. FIG. 4a is an elevation view of the embodiment of ferrule 20 that is shown in FIG. 1. FIGS. 8b –8g are elevation views showing additional exemplary embodiments of ferrules 120, 320, 420, 520, 620, 720, 820, 920, 1020, 1120 and 1220 in accordance with the invention. In FIGS. 4a, 8a–8l of the ferrule 20 through 1220, the reference numerals of common features have the same last two digits (e.g., heads 22 through 722) for convenience in interpreting the drawings.

Referring first to FIG. 8a, ferrule 220 may be formed of titanium or other suitably hard material Kel-F$^R$ brand polychlorotriflouroethylene (PCTFE), marketed by the 3M corporation). Ferrule 220 must be made from a material hard enough to provide inner support for tubing 64, so that the tubing cold flows when compressed between ferrule 220 and nut 70 (or sleeve 50 if sleeve 50 is used). Titanium and PCTFE have the additional advantage of being non-reactive. Ferrule 220 has a tapered head 222 that seats against the device 18 and terminates in a sharp edge 234. In the exemplary ferrule 220 head 222 is conical. Ferrule 220 has a tapered tail 226 terminating in a sharp edge 232. The exemplary tail 226 is also conical. A body 224 integrally connects head 222 and tail 226. Ferrule 220 has an axial passage 228 that may be larger in diameter than the inside diameter 65 of the tubing 64 by between 0.003 and 0.004 inches. Ideally, the ferrule inside diameter (ID) is the same as the tubing ID 65. Because there are variations in the tubing diameter, it may be more practical to make the inside diameter 228 of ferrule 220 equal to the upper limit on the size of the tubing ID 65. It is preferable for passage 228 to be slightly larger than tubing ID 64, than for passage 228 to be smaller.

The tail 226 of ferrule 220 terminates in a sharp edge (i.e., not rounded) that forms an acute angle, preferably 15 degrees (i.e., angle 25 shown in FIG. 4a is 165 degrees) with respect to the longitudinal axis of ferrule 520. The acute conical shape forces the tubing 64 material into compression when tubing 64 is pushed onto ferrule 220. The tubing 64 material is thus cold flowed. After nut 70 is tightened to seal the fitting, the cold flow continues. Tubing 64 material creeps forward to fill the space provided forward of tail 226. As described below, there are many embodiments of ferrule 226 that provide space along the body 224, into which space the material is cold flowed.

Referring now to FIG. 3c, an enlarged cross-section of an exemplary ferrule head 22 is shown in its chamfered sealing surface 16. It is understood that the respective heads 22 through 722 are similar in each respective embodiment of ferrule 20 through 720 as shown in FIGS. 8a–8k; the description of the head 222 is not repeated for each embodiment. Before coupling nut 70 is tightened, head 22 has an angle 12 with respect to the longitudinal axis of ferrule 20, as shown in phantom by surface 22. Sealing surface 16 has a respective angle 14 with respect to the same axis. Angle 12 is less than angle 14. The difference between angle 12 and angle 14 is very small (typically a fraction of a degree), so that head 22 deforms to fit sealing surface 16, as shown by surface 22a in FIG. 3c.

The sharp edge 34 deforms elastically when nut 70 is tightened, forming a tight seal between head 22 and sealing surface 16 of device 18. Because the deformation is below the proportional limit of the material, ferrule 20 substantially returns to its original shape when removed from device 18, and is reusable. Once coupling nut 70 pushes ferrule 20 against seat 16, nut 70 may be subjected to large torques without any unfavorable effect. Increasing the torque further on nut 70 compresses head 22, but does not affect the position of the ferrule 20 or sleeve 50 substantially.

Ferrule 20, as shown in FIG. 4a, also includes a groove 30, into which the tubing material flows when the assembly is installed. This groove is discussed above with reference to FIG. 3b. A shoulder 36 separates groove 30 from tail 26.

Referring now to FIG. 8b, another embodiment of ferrule 120 is shown. Ferrule 120 includes the features of Ferrule 220, as shown in FIG. 8a. Ferrule 120 includes at least one land 121a, for gripping tubing 64. The exemplary ferrule 120 includes two lands 121a and 121b. When tubing 64 is forced over lands 121a and 121b, the tubing material flows from the location of the lands 121a and 121b to region 125 between the lands, to region 126, and to a region surrounding body 124.

FIG. 8c shows another embodiment of ferrule 320, in which the groove 330 is located immediately adjacent to the tail 26. Groove 330 of ferrule 320 also has a rectangular cross section, as compared to groove 30 in FIG. 4a, which has a trapezoidal cross section. The rectangular cross section of groove 330 provides additional space into which the material of tubing 64 flows.

FIG. 8d shows an embodiment of ferrule 420 having two grooves 430 and 442 separated by a shoulder 424. The additional groove 442 provides additional gripping ability.

Figure 8E:
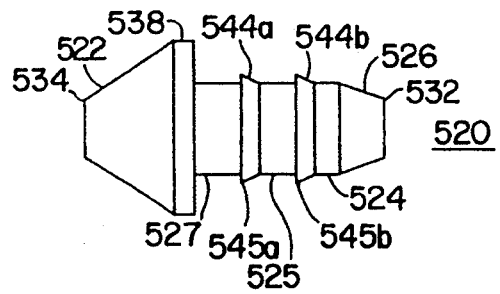

FIG. 8e shows an embodiment of ferrule 520. This embodiment of ferrule 520 has at least one circumferential barb 544a. Exemplary ferrule 520 has two barbs 544a and 544b for gripping the internal surface of tubing 64. The barbs 544a and 544b have an effect similar to that of the groove 30 shown in FIG. 4a. A region 525 of ferrule 520 has a diameter that is smaller than the diameter of either barb 544a, 544b. When tubing 64 is forced over the barbs 544a and 544b, and the coupling nut 70 tightened, material flows from the region in which barbs 544a and 544b are located to the regions 527 and 525 in front of the respective barbs 544a and 544b.

The barbed embodiment of FIG. 8e has advantages and disadvantages relative to the grooved embodiment of FIG. 4a. The barb 544a provides greater resistance to prevent tubing 64 from pulling off of ferrule 520. On the other hand, more effort is required to push tubing 64 over barb 544a of ferrule 520, relative to the grooved ferrule 20. A small (e.g., approximately 0.02 inches) flat circumferential surface 545a, 545b may be placed at the edge of each barb, as shown in FIG. 8e.

Figure 8F:
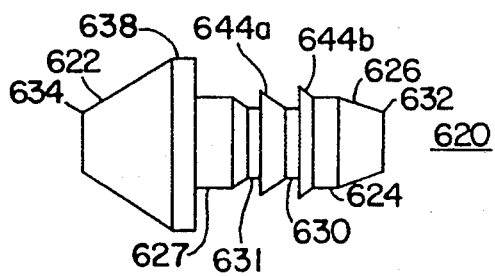

FIG. 8f shows another embodiment of the ferrule 620, having two barbs 644a and 644b, and two grooves 631 and 630, each in front of a respective barb. The grooves provide additional space into which the tubing material flows.

Figure 8G:
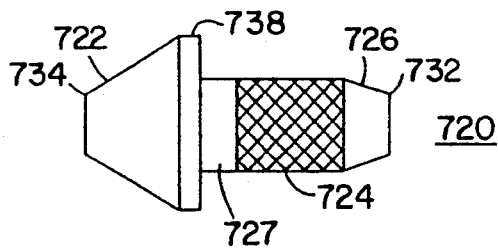

FIG. 8g shows another embodiment of the ferrule 720, having a knurled surface 724. The tubing material flows into the crevices of the knurled surface 724, so that the tubing is effectively gripped.

Figure 8H:
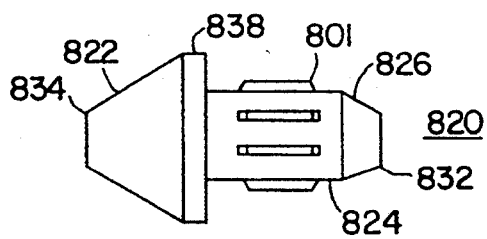

FIG. 8h shows another embodiment of the ferrule 820, in which the body 824 includes a plurality of axial splines 801 for gripping the internal surface 65 of the tubing 64.

Figure 8I:
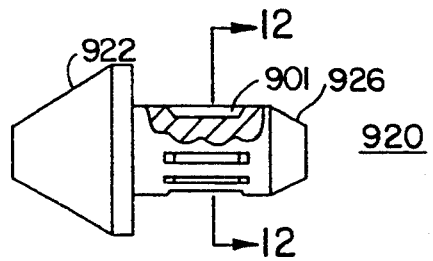
Figure 12:
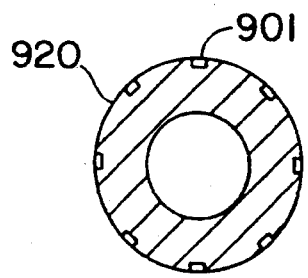
FIG. 12 is a cross sectional view of the ferrule shown in FIG. 8i.

FIGS. 8i and 12 show another embodiment of the ferrule 920, in which the body 924 includes a plurality of axial slots 901 for receiving the compressed tubing.

Figure 8J:
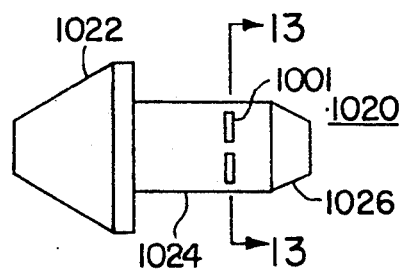
Figure 13:
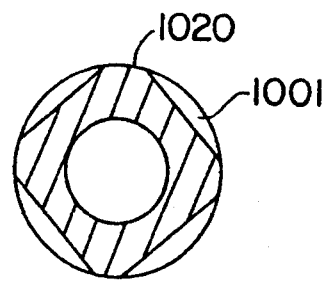
FIG. 13 is a cross sectional view of the ferrule shown in FIG. 8j.

FIGS. 8j and 13 show an additional embodiment of the ferrule 1020, in which the body 1024 includes a plurality of circumferential slots 1001 for receiving the compressed tubing 64. Slots 1001 are flat, and may, for example, be machined into body 1024 by milling.

Figure 8K:
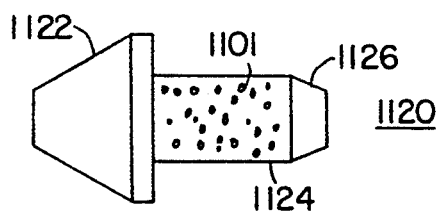

FIG. 8k shows a ferrule 1120 in which body 1124 has been roughened to grip the inner surface 65 of tubing 64. The surface of body 1124 may, for example, be roughened by sandblasting or machining.

Figure 4B:
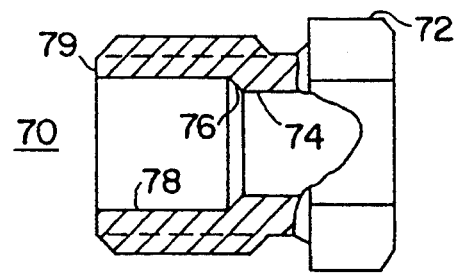
FIG. 4b is a partial cross sectional view of the coupling nut shown in FIG. 2d.

Generally, any of the embodiments of ferrule 20–720 may be used in combination with any of the variations of nut 70, sleeve 50, and holder 80. If ferrule 20 is to be used without sleeve 50, then nut 70 (FIG. 4b) is preferable to nut 170 (FIG. 10a), because the geometry of nut 70 is better suited to cold flowing tubing 64 to provide a secure joint. Also, if the barbed ferrules 520 (FIG. 8e) or 620 (FIG. 8f) are used, then the collapsible sleeves 550 (FIGS. 9e and 9f) and 650 (FIGS. 9g and 9h) should not be used, as explained in detail below with reference to FIGS. 9e–9h.

Figure 8L:
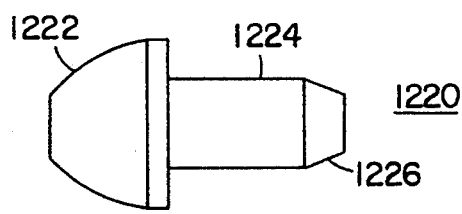

Other variations of the ferrule are contemplated. For example, although tapered head 22 and tail 26 have been described as conical in shape, other tapered profiles (e.g., truncated spherical or paraboloid in shape) may also be used for the head, so long as a sharp edge 32 is provided at the end of tail 26, to ensure substantially no carryover. For example, FIG. 8l shows a ferrule 1220 having a head 1222 in the form of a paraboloid. In another variation (not shown), a metal washer may be placed behind the head of a plastic ferrule to provide a hard bearing surface. The front surface 79 of coupling nut 70 engages the washer to push the ferrule forward. If a plastic (e.g., PCTFE) ferrule is used, the head may have a non-tapered shape. For example, a flat plastic head may be used to couple tubing 64 to a suitably shaped sealing surface on the device.

The Holder

Figure 5A:
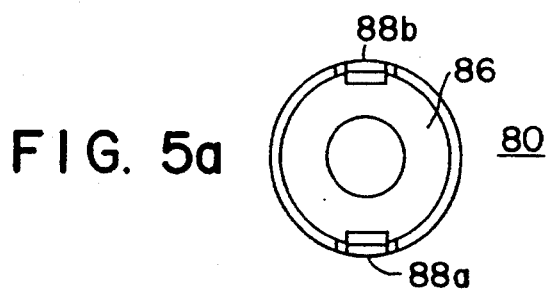
FIGS. 5a and 5b are plan and elevation views of the protective ferrule holder shown in FIG. 2d.
Figure 5B:
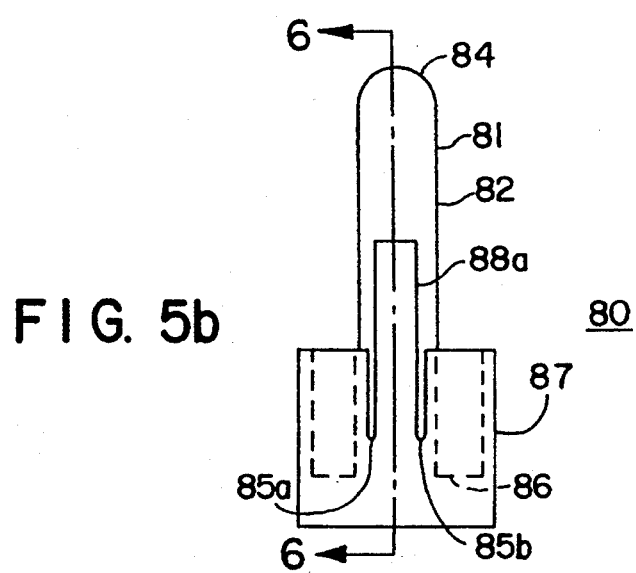

FIGS. 5a and 5b are plan and elevation views of holder 80, which is shown in the storage configuration in FIG. 2a. Holder 80 may be formed of a variety of materials, preferably hard, plastic. In its storage configuration, ferrule 20 is retained in holder 80 by latches 88a and 88b (as shown in FIG. 2a). Holder 80 has a front wall 86 against which the head 22 of the ferrule 20 seats. A side wall 87 (shown in FIG. 5b) substantially surrounds the head 22 of ferrule 20 to protect the head 22. Holder 80 has a shaft 81 that extends through the axial passage 28 of ferrule 20. Shaft 81 has a proximal portion 82 and a tip 84. The proximal portion 82 of the shaft is longer than ferrule 20, and larger in diameter than the inside diameter 65 of tubing 64. When shaft 81 is inserted into tubing 64, the proximal portion 82 of shaft 81 straightens and aligns the tubing 64.

Preferably, holder 80 has slots 85a and 85b. When ferrule 20 is installed in holder 80, slots 85a and 85b allow the user to view the side of head 22 and body 24 of ferrule 20. Slots 85a and 85b make it easier to bend latches 88a and 88b, to release ferrule 20 from holder 80.

FIG. 6 is a cross sectional view of the holder shown in FIGS. 5a and 5b. FIG. 7 shows an alternative embodiment of the holder 90. Holder 90 is similar to holder 80 in all respects except for the shape of shaft 91. Shaft 81, as shown in FIG. 6, has a uniform diameter along its proximal portion 82, all the way to tip 84. In contrast, shaft 92 of holder 90 (shown in FIG. 7) also has a distal portion 97. Distal portion 97 has a smaller diameter than the ID 65 of tubing 64. The reduced diameter of distal portion 97 makes it easy to insert in tubing 64. A middle portion 93 integrally connects proximal portion 92 and distal portion 97. Middle portion 93 is tapered to facilitate leading the tubing over tail 26 of ferrule 20. Preferably, the angle 95 of the taper is the same as the taper angle 25 of tail 26. It is also preferable to have the length of ferrule 20 be the same as the length of proximal portion 82. According to this aspect of the invention, middle portion 93 and tail 26 provide a substantially continuous tapered surface for stretching tubing 64 over ferrule 20.

Although tool 180 (FIG. 1a) is shown with a shaft 181 in the form of shaft 81 of FIG. 6, tool 180 may also have a shaft (not shown) in the form of shaft 91, as shown in FIG. 7. Tool 181 performs the same function as holder shafts 81 (FIG. 6) and 91 (FIG. 7) during installation of the fitting.

The Sleeve

Figure 4C:
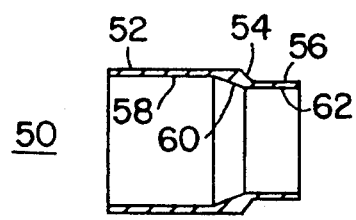
FIG. 4c is a cross sectional view of the sleeve shown in FIG. 2d.

FIG. 4c is a cross section of an exemplary sleeve 50 that may optionally be included in the fitting. Sleeve 50 may be formed of type 303 stainless steel or other suitable material. Sleeve 50 has a shouldered outer surface 54 and a ramped inner surface 60 integrally connecting the internal diameters of forward and rearward sections 58 and 62. Ramped inner surface 60 is greater in inside diameter towards the forward end of the sleeve and smaller in inside diameter towards the rearward end of the sleeve. Sleeve 50 includes a rearward section 62 integrally connected to the smaller rearward end of ramped inner surface 60. Sleeve 50 may have a forward section 58 integrally connected to the larger forward end of ramped inner surface 60, as shown. The forward section 58, ramped section 60 and rearward section 62 have respective outer surfaces 52, 54 and 56.

As shown in FIG. 3a, the forward section 58 of sleeve 50 is short enough so that the forward end of sleeve 50 does not contact head 22 of ferrule 20 when the fitting is installed. An annular space 17 is formed, having head 22 in front, sleeve 50 in back, tubing 64 radially inside and nut 70 radially outside. This annular space provides additional room into which the tubing material flows. The inventor has determined that by providing this additional space into which the tube material may flow, annular space 17 avoids egress of tube material between the head 22 of ferrule 20 and the front surface 79 of nut 70. Tubing material fragments that escape between front surface 70 and head 22 are likely to remain in the chamfered sealing surface 16 after ferrule 20 is removed, which is undesirable.

Sleeve 50 performs two functions. The first function is to compress the tubing so that it is gripped by the fitting. Tubing 64 is compressed between ramped inner surface 60 of sleeve 50 and tail 26 of ferrule 20, as shown in FIG. 3b. In particular, tubing 64 is compressed the most adjacent to corner 61 in sleeve 50. The tubing material then flows forward of the reduced diameter section between tapered internal surface 60 and tail 26 into region 68. The tubing cross section is greater in region 68, forward of corner 61, so that tubing 64 is held firmly by the fitting. If a ferrule 20 that has a groove 30 is used, then the material is squeezed further out to fill or partially fill groove 30.

The second function of the sleeve is to prevent nut 70 from twisting tubing 64 when nut 70 is tightened. In the embodiment shown in FIG. 1c, in which no sleeve is used, torque is transmitted from nut 70 to tubing 64, twisting the tubing. This may be undesirable, particularly in short tube lengths. As shown in FIG. 3a, sleeve 50 is engaged by an inner surface 76, which may be a ramp or a shoulder within nut 70, forcing sleeve 50 forward towards head 22 of ferrule 20. The friction force between the sleeve 50 and tubing 64 is greater than the friction force between sleeve 50 and nut 70, so that torque is not transmitted from nut 70 to tubing 64.

Figure 9A:
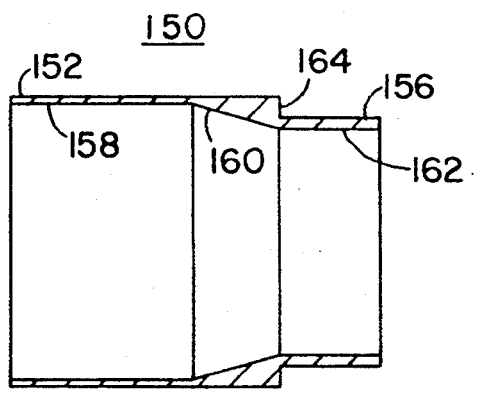
FIGS. 9a-9d are cross sectional views of variations of the sleeve shown in FIG. 4c.
Figure 10A:
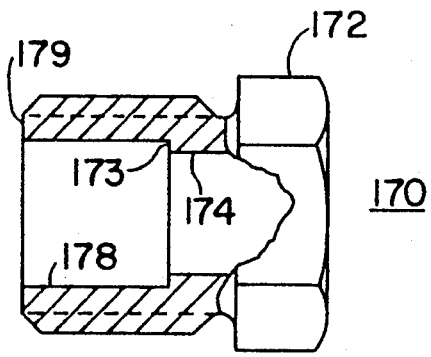
FIGS. 10a and 10b are partial cross sectional view of variations of the nut shown in FIG. 4b.

As with ferrule 20, many variations and embodiments of sleeve 50 are contemplated. For example, FIG. 9a is a cross sectional view of a sleeve 150 in which there is no tapered outer surface. The outer surface surrounding tapered surface 160 has the same diameter as the outer surface 152 of the forward section. A shoulder 164 is located between the tapered section 160 and the rearward section 162. Sleeve 150 is received by an alternate coupling nut 170, as shown in FIG. 10a. Nut 170 has a bore 178 sized to receive sleeve 150.

Figure 9B:
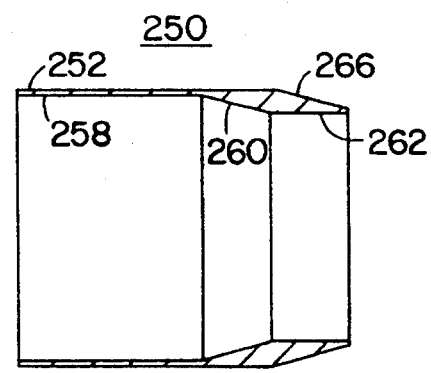
Figure 9C:
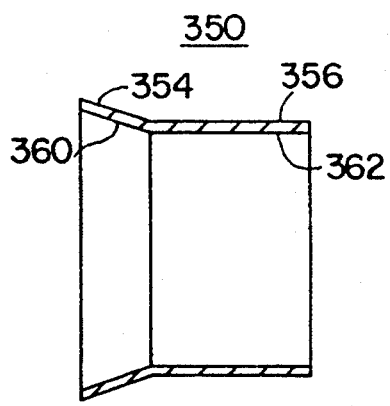
Figure 9D:
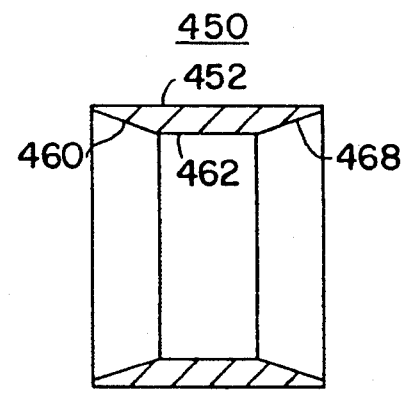

FIGS. 9b–9d show additional variations of sleeve 50. FIG. 9b is a cross section of another sleeve 250, that has a tapered outside surface 266 on its rearward section 262. FIG. 9c is a cross section of a sleeve 350 that has only a tapered section and a rearward section. FIG. 9d is a cross section of a sleeve 460 having a single outside diameter. A front ramped section 462 and a rear ramped section 468 are provided. The embodiment of FIG. 9d is symmetric, so that it cannot be installed backwards.

Figure 9E:
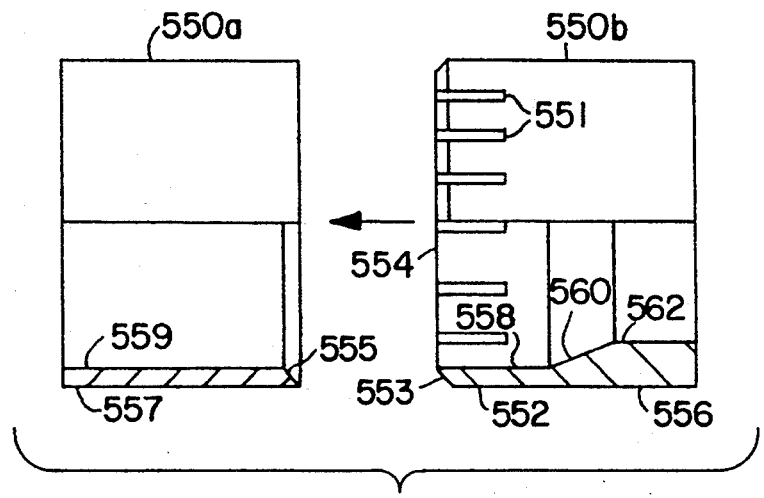

FIGS. 9e and 9f show another exemplary sleeve 550. Sleeve 550 is formed from two distinct pieces 550a and 550b, as shown in partial cross section in FIG. 9e. Sleeve piece 550a comprises a cylindrical shell 559 having an internally chamfered end 555. Sleeve piece 550b includes a forward section 558, a tapered section 560 and a rearward section 562. The three sections may have the same outside diameter 552, as shown. The forward end of the outside surface 552 includes a beveled edge 553. Chamfer 555 is sized to receive beveled edge 553. A plurality of longitudinal slots 551 (parallel to the axis of sleeve 550) are spaced equally about the circumference of a portion at the forward end of piece 550b. A plurality of members 554 are formed between the slots.

Sleeve 550 is slipped over tubing 64 before tubing 64 is placed on ferrule 20, in a manner similar to that described above with reference to FIG. 2b.

FIG. 9f is a partial cross section showing sleeve 550 as it appears after assembly. Unlike sleeve 50, sleeve 550 is long enough so that the front edge of piece 550a contacts head 22 of ferrule 20 when nut 70 is tightened. Once piece 550a contacts head 22, advancing nut 70 further pushes the portion at the forward end of section 558 into piece 550a. The beveled edge 553 guides the portion, including members 554, into chamfer 555. Slots 551 allow the members 554 to bend more easily. As the portion, including members 554, bends radially inward, members 554 grip the outside of tubing 64 securely. Any tension tending to pull tubing 64 out would cause members 554 to dig into the tubing material more securely.

FIGS. 9g and 9h show a further embodiment of the sleeve 650. FIG. 9g shows sleeve 650 before installation. Sleeve 650 has the form of a single cylindrical shell. A forward section 658, a tapered section 660 and a rearward section 662 are provided, with respective outer surface areas 652, 654 and 656. The inner surface of forward section 658 has two circumferential grooves 661a and 661b. Grooves 661a and 661b are connected by a plurality of equally spaced longitudinal slots 651 that are parallel to the axis of sleeve 650. Members 667a and 667b are formed between each pair of slots, the members 667a and 667b separated by groove 663. A third circumferential groove 663 is located on the outer surface 652 of forward section 658, approximately midway between grooves 661a and 661b. As shown in FIG. 9g, the two inner grooves 661a and 661b and the outer groove 663 provide a parallelogram shaped cross section for members 667a and 667b.

FIG. 9h shows sleeve 9h after force is applied by nut 70. Like sleeve 550 in FIG. 9f, sleeve 650 is long enough so that the forward end of sleeve 650 contacts head 22 when the fitting is assembled. When nut 70 is advanced far enough so that sleeve 650 contacts head 22, further tightening of nut 70 causes the portion including members 667a and 667b to bend inward radially. As the portion including members 667a and 667b bends inward, members 667a and 667b grip the tubing and squeeze the tubing against body 24 of ferrule 20.

FIG. 9i is a cross sectional view of a sleeve 750 in which the inner surface 760 is a shoulder (as compared to the ramped inner surface 60 of sleeve 50, as shown in FIG. 4c).

Figure 14:
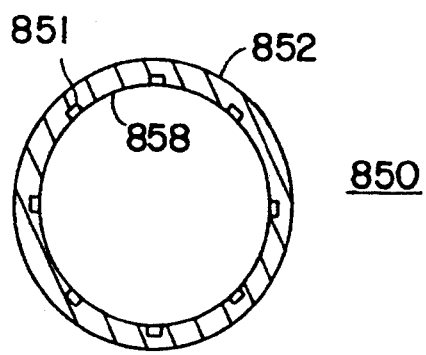
FIG. 14 is a cross sectional view of the sleeve shown in FIG. 9j.

FIGS. 9j and 14 are cross sectional views showing another variation of the sleeve 850. Sleeve 850 includes a plurality of axial slots 851 for receiving the compressed tubing 64, when the tubing is cold flowed by tightening coupling nut 70.

Other variations of sleeve 50 are contemplated. For example, instead of the continuous, cone shaped ramped inner surface 60 shown in FIG. 4c, the ramped inner surface may be formed by a plurality of ramped axial splines (not shown).

Generally, any of the variations of ferrule 20 shown in FIGS. 8a-8l may be assembled with any of the sleeves shown in FIGS. 9a-9h. The exception is that the collapsing (bendable) sleeves 550 and 650 shown in FIGS. 9e-9h should not be used with the barbed ferrules 520 and 620 shown in FIGS. 8e and 8f, or the splined ferrule 920, shown in FIG. 8h. The combination of the raised barbs 544a, 544b on ferrule 520 and the collapsing members 554 on sleeve 550 could result in perforation of tubing 64. Similarly, the combination of the raised splines 801 and the collapsing members 554 on sleeve 550 could result in perforation of tubing 64.

The Coupler

Figure 10B:
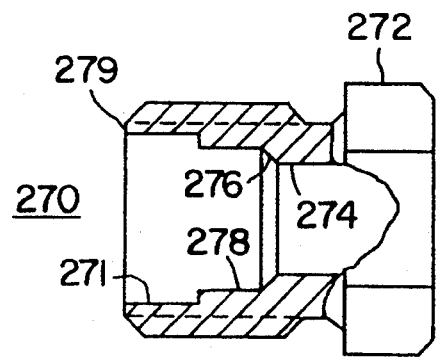

FIGS. 10a and 10b are partial cross sections of two variations of coupling nut 70. As shown in FIG. 10a, coupling nut 170 has an inner surface 173 in the form of a shoulder. Generally, nut 170 is functionally equivalent to nut 70, however, a greater tensile load may be accommodated without causing tubing 64 to fail if nut 70 is used, with its ramped inner surface 76.

FIG. 10b shows another variation of the coupling nut 270, in which a counterbore 271 is provided to receive the tubing material.

Although coupler 70 has been described in the form of a coupling nut 70, it is understood that the invention may be practiced using a variety of fastening techniques in place of a threaded coupler 70. For example, instead of having an outer thread, coupler 70 may be smooth, and an over center spring clamp or a plurality of small screws may be used to secure the coupler 70 to the device. Also, a washer may be placed between front surface 79 of coupler 70 and the head 22 of the ferrule 20.

It is understood by one skilled in the art that many variations of the embodiments described herein are contemplated. While the invention has been described in terms of exemplary embodiments, it is contemplated that it may be practiced as outlined above with modifications within the spirit and scope of the appended claims.

What is claimed:

1. A fitting assembly for coupling tubing to a device having a sealing surface, comprising:
    a ferrule for seating against the sealing surface, the ferrule having an inside diameter substantially equal to an inside diameter of the tubing, the ferrule having a head, a body and a tail, the tail having a knife sharp edge, the edge having a cross-section that terminates in a single acute angle, whereby formation of a non-flushable volume adjacent to the tail and retention of a fluid therein are prevented;
    coupling means for engaging the ferrule to push the head against the sealing surface, the coupling means including an inner surface, wherein a region is defined between the coupling means and the body of the ferrule, and the tubing material is compressed between the tail of the ferrule and the inner surface, causing the compressed tubing material to flow into the region.

2. A fitting assembly in accordance with claim 1, wherein the inner surface is selected from the group consisting of a ramp and a shoulder.

3. A fitting assembly in accordance with claim 1, wherein the body includes an annular groove, and the tubing creeps to fill the groove when tubing is compressed between the tail of the ferrule and the inner surface.

4. A fitting assembly in accordance with claim 1, wherein the body of the ferrule is knurled to grip the inside of the tubing.

5. A fitting assembly in accordance with claim 1, wherein the body includes a barb for gripping the internal surface of the compressed tubing.

6. A fitting assembly in accordance with claim 1, wherein the body includes a land that grips the tubing.

7. A fitting assembly in accordance with claim 1, wherein the body includes a plurality of axial splines for gripping the internal surface of the tubing.

8. A fitting assembly in accordance with claim 1, wherein the body includes a plurality of axial slots for receiving the compressed tubing.

9. A fitting assembly in accordance with claim 1, wherein the body includes a plurality of circumferential slots for receiving the compressed tubing.

10. A fitting assembly in accordance with claim 1, wherein the body includes means for gripping the internal surface of the tubing.

11. A fitting assembly in accordance with claim 1, wherein the coupling means include a counterbore for receiving the compressed tubing material.

12. A fitting assembly for coupling tubing to a device having a sealing surface, comprising:
    a ferrule for seating against the sealing surface, the ferrule having a head, a body and a tapered tail;
    a sleeve having an inner surface selected from the group consisting of a shoulder and a ramp that is greater in inside diameter towards a forward end of the sleeve and smaller in inside diameter towards a rearward end of the sleeve, the tubing being compressed between the tail of the ferrule and the inner surface of the sleeve to cold flow the tubing without any permanent deformation of the sleeve, so that the tubing flows into a region defined between the inner surface and the body; and
    a coupler for engaging the head of the ferrule to push the ferrule against the sealing surface, and for engaging the sleeve to push the sleeve forward without any permanent deformation of the sleeve, the forward end of the sleeve extending toward the head and forming a separation between the sleeve and the ferrule when the coupler engages the head of the ferrule.

13. A fitting assembly in accordance with claim 12, wherein the sleeve includes a forward section connected to the inner surface, and the forward section of the sleeve includes a portion having a plurality of slots positioned symmetrically about a circumference of the sleeve, the slots being parallel to an axis of the sleeve.

14. A fitting assembly in accordance with claim 13, wherein the slotted portion is adapted to bend inward radially for gripping the tubing when the coupling means pushes the sleeve forward.

15. A fitting assembly in accordance with claim 14, wherein the forward section of the sleeve includes first and second pieces, the first piece terminating at a forward end of the slotted portion, the second piece being a cylindrical shell.

16. A fitting assembly in accordance with claim 15, wherein the forward end of the first piece is beveled, and a rearward end of the second piece is internally chamfered to receive the beveled forward end of the first piece.

17. A fitting assembly in accordance with claim 14, wherein the slotted portion includes an annular groove on its outer surface, the groove being substantially centered between a forward end and a rearward end of the portion.

18. A fitting assembly in accordance with claim 17, wherein the slotted portion includes two annular grooves on its inner surface, the respective grooves being located at the forward and rearward ends of the portion.

19. A fitting assembly in accordance with claim 12, wherein the sleeve includes a plurality of axial slots for receiving the compressed tubing.

20. A low carryover fitting assembly for coupling tubing to a device having a sealing surface, comprising:
   a ferrule having a tapered head for seating against the sealing surface, a body and a tail, the ferrule having an axial passage that is substantially equal in diameter to the inside diameter of the tubing;
   a sleeve having a cylindrical forward section, a cylindrical rearward section and a middle section therebetween, the middle section having a ramped inner surface that is greater in inside diameter towards the forward section and smaller in inside diameter towards the rearward section; and
   a coupling nut having a front surface that engages the head of the ferrule to push the head against the sealing surface and an inner shoulder that engages the rearward section of the sleeve to move the sleeve towards the head when the coupling nut is tightened, thereby compressing the tubing between the tail and the inner surface, so that the compressed tubing flows into a region defined between the inner surface and the body.

21. In a fitting assembly for coupling tubing to a device, apparatus comprising:
   a ferrule having a head for seating against the device, a body having means for gripping an internal surface of the tubing, and a conical tail terminating in a sharp edge, the edge having a cross section that terminates in a single acute angle, the ferrule having an axial passage extending throughout its length, the axial passage having an inner diameter substantially equal to an inner diameter of the tubing, whereby formation of a non-flushable volume adjacent to the tail and retention of a fluid therein are prevented; and
   a holder having a side wall that substantially surrounds the head of the ferrule for protecting the head, and a shaft that extends through the axial passage of the ferrule, the shaft being longer than the ferrule and projecting from the tail of the ferrule, the shaft being substantially equal in diameter to the inner diameter of the tubing, wherein the shaft aligns the tubing, and the tubing is positioned on the shaft over the sharp edge and the body of the ferrule, and the internal surface of the tubing has no cut, chamfer, gouge or sharding.

22. Apparatus in accordance with claim 21, wherein the shaft includes a proximal portion that is substantially equal in diameter to the inside diameter of the tubing and a distal portion that is smaller in diameter than the inside diameter of the tubing, wherein the distal portion of the shaft adapted to be inserted in the tubing to guide the tubing to the proximal portion of the shaft.

23. Apparatus in accordance with claim 22, wherein the proximal portion is substantially equal in length to the ferrule.

24. Apparatus in accordance with claim 23, wherein the shaft includes a middle portion integrally connecting the proximal portion and the distal portion, the middle portion having an outer surface which forms a first angle with respect to a longitudinal axis of the shaft, the first angle being substantially equal to a second angle between an outer surface of the tail of the ferrule and the axial passage.

25. A method for attaching tubing to a device, comprising the steps of:
   (a) positioning a ferrule having a tail and a body on a shaft of a holder, so that the shaft projects from the tail of the ferrule;
   (b) forcing the tubing over the tail and the body of the ferrule;
   (c) sliding a coupler over the tubing and the tail and body of the ferrule, until the coupler engages a head of the ferrule;
   (d) inserting the ferrule and coupler into a mating receptacle in the device; and
   (e) advancing the coupler in the receptacle so that the head of the ferrule seats firmly against the device, and the tubing around the tail of the ferrule is compressed, whereby the tubing material around the tail flows to a region between an inner surface of the coupler and the body of the ferrule.

26. A method in accordance with claim 25, further comprising forcing the tubing over the shaft between positioning the ferrule on the shaft and forcing the tubing over the tail.

27. A method in accordance with claim 26, further comprising removing the ferrule and tubing from the holder after forcing the tubing over the tail and the body of the ferrule.

28. A method in accordance with claim 25, further comprising positioning the ferrule on a shaft of a tool so that the shaft projects from the tail of the ferrule, before forcing the tubing over the tail.

29. A fitting assembly according to claim 20, wherein the body of the ferrule includes means for gripping the tubing.

30. A method for attaching tubing to a device, comprising the steps of:
   (a) forcing the tubing over a tail and a body of a ferrule;
   (b) sliding a sleeve over the tubing and the tail and body of the ferrule;

(c) sliding a coupler over the tubing, the sleeve and the tail and body of the ferrule, until the coupler engages a head of the ferrule;

(d) inserting the ferrule and coupler into a mating receptacle in the device; and (e) advancing the coupler in the receptacle so that the head of the ferrule seats firmly against the device, and the tubing around the tail of the ferrule is compressed, whereby the tubing material around the tail flows to a region between the sleeve and the body of the ferrule.

31. A fitting assembly according to claim 10, wherein the gripping means grips the tubing without any permanent deformation of the ferrule or the coupling means, whereby the ferrule and the coupling means are reusable.

32. A fitting assembly according to claim 12, wherein an annular space is formed between the sleeve and the head of the ferrule, and the compressed tubing flows into the annular space when the coupler engages the head of the ferrule.

33. A fitting assembly for coupling tubing to a device having a sealing surface, comprising:

a ferrule for seating against the sealing surface, the ferrule having an inside diameter substantially equal to an inside diameter of the tubing, the ferrule having a head, a body and a tail, the tail having a knife sharp edge, the edge having a cross-section that terminates in a single acute angle, whereby formation of a non-flushable volume adjacent to the tail and retention of a fluid therein are prevented;

a detachable ferrule holder having a shaft that projects from the tail of the ferrule and has a diameter substantially equal to the inside diameter of the tubing, so that the shaft aligns the tubing with the tail and the body of the ferrule, and an internal surface of the tubing has no cut, chamfer, gouge or sharding; and coupling means for engaging the ferrule to push the head against the sealing surface, the coupling means including an inner surface, wherein a region is defined between the coupling means and the body of the ferrule, and the tubing material is compressed between the tail of the ferrule and the inner surface, causing the compressed tubing material to flow into the region.

34. A fitting according to claim 33, wherein the acute angle is approximately 15 degrees.

35. A fitting according to claim 33, wherein the head of the ferrule is tapered and has a cross section that terminates in a single acute angle.

36. A method in accordance with claim 30, wherein step (d) includes bending a portion of the sleeve radially inward to grip the tubing.

* * * * *